US008178845B2

(12) United States Patent  
Zeng

(10) Patent No.: US 8,178,845 B2
(45) Date of Patent: May 15, 2012

(54) COLLIMATOR AND RELATED METHODS

(75) Inventor: Gengsheng Lawrence Zeng, Holladay, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 427 days.

(21) Appl. No.: 12/479,731

(22) Filed: Jun. 5, 2009

(65) Prior Publication Data

US 2010/0308226 A1 Dec. 9, 2010

(51) Int. Cl.
*G21K 1/02* (2006.01)
(52) U.S. Cl. .................................. 250/363.1
(58) Field of Classification Search ............. 250/363.01, 250/363.02, 363.03, 363.04, 363.05, 363.1, 250/505.1
See application file for complete search history.

(56) References Cited

U.S. PATENT DOCUMENTS 4,250,392 A * 2/1981 Leask et al. ............... 250/505.1
2008/0304619 A1* 12/2008 Blevis et al. .................. 378/16

OTHER PUBLICATIONS

Patton JA, et al."D-SPECT: a new solid state camera for high speed molecular imaging" J Nucl Med., vol. 47 (suppl 1), p. 189P, 2006.
Rogers WL, et al., "SPRINT II: a second generation single photon ring tomography for brain imaging" IEEE Trans. Med. Imag., vol. 7, pp. 291-297, 1988.
Chang W, et al. "Design concepts and potential performance of MarC-SPECT—A high-performance cardiac SPECT system" J. Nucl Med., vol. 47 (supplement 1), p. 190P, 2006.
Funk T, et al. "Evaluation of multipinhole collimators for cardiac SPECT" J. Nucl Med., vol. 48 (suppl 2), p. 161P, 2007.
Funk T, et al. "A novel approach to multipinhole SPECT for myocardial perfusion imaging" J. Nucl Med., vol. 47, pp. 595-602, 2006.
Kirch DL, et al. "Modification of a triple-head rotational SPECT (R-SPECT) system to perform stationary multi-pinhole SPECT (MP-SPECT) for myocardial perfusion imaging" J. Nuc. Med., vol. 48 (suppl 2), p. 161P, 2007.
Steele PP, et al., "Comparison of simultaneous dual-isotope multipinhole SEPCT with rational SPECT in a group of patients with coronary artery disease" J. Nuc. Med., vol. 49, pp. 1080-1089, 2008.
Rohmer D, et al., "The effect of truncation on very small cardia SPECT camera systems" J Nucl Med., vol. 47 (suppl 1), p. 64P, 2006.
Xiao J, et al., "Small field-of-view dedicated cardiac SPECT systems: Impact of projection truncation" J Nucl. Med., vol. 48 (suppl 2), p. 48P, 2007.
Gullberg GT, et al., "Review of convergent beam tomography in single photon emission computed tomography" Phys. Med. Biol., vol. 37, pp. 507-534, 1992.
Lange AK, et al., "EM reconstruction algorithms for emission and transmission tomography" J. Comput. Assist. Tomogr., vol. 8, pp. 306-316, 1984.
Hudson HM, et al., "Accelerated EM reconstruction using ordered subsets" J. Nucl. Med., vol. 33, p. 960, 1991.
Hudson HM, et al., "Accelerated image reconstruction using ordered subsets of projection data" IEEE Trans. Med. Imag., vol. 13, pp. 601-609, 1994.
Huang Q, et al.,"An analytical algorithm for skew-slit imaging geometry with non-uniform attenuation correction" Med. Phys., vol. 33, No. 4, pp. 997-1004, 2006.
Tang Q, et al., "Analytical algorithm for skew-slit collimator SPECT with uniform attenuation correction" Phys. Med. Biol., vol. 51, pp. 6199-6211, 2006.

* cited by examiner

*Primary Examiner* — Mark R Gaworecki
(74) *Attorney, Agent, or Firm* — James W. Hill; M. Todd Hales; McDermott Will & Emery LLP

(57) ABSTRACT

A collimator and related methods are shown and described. The collimator can be a multi-divergent-beam collimator having a plurality of inverted, ordered sections of a cone-beam collimator reassembled in a substantially reversed order relative to the ordering of the cone-beam collimator.

19 Claims, 10 Drawing Sheets

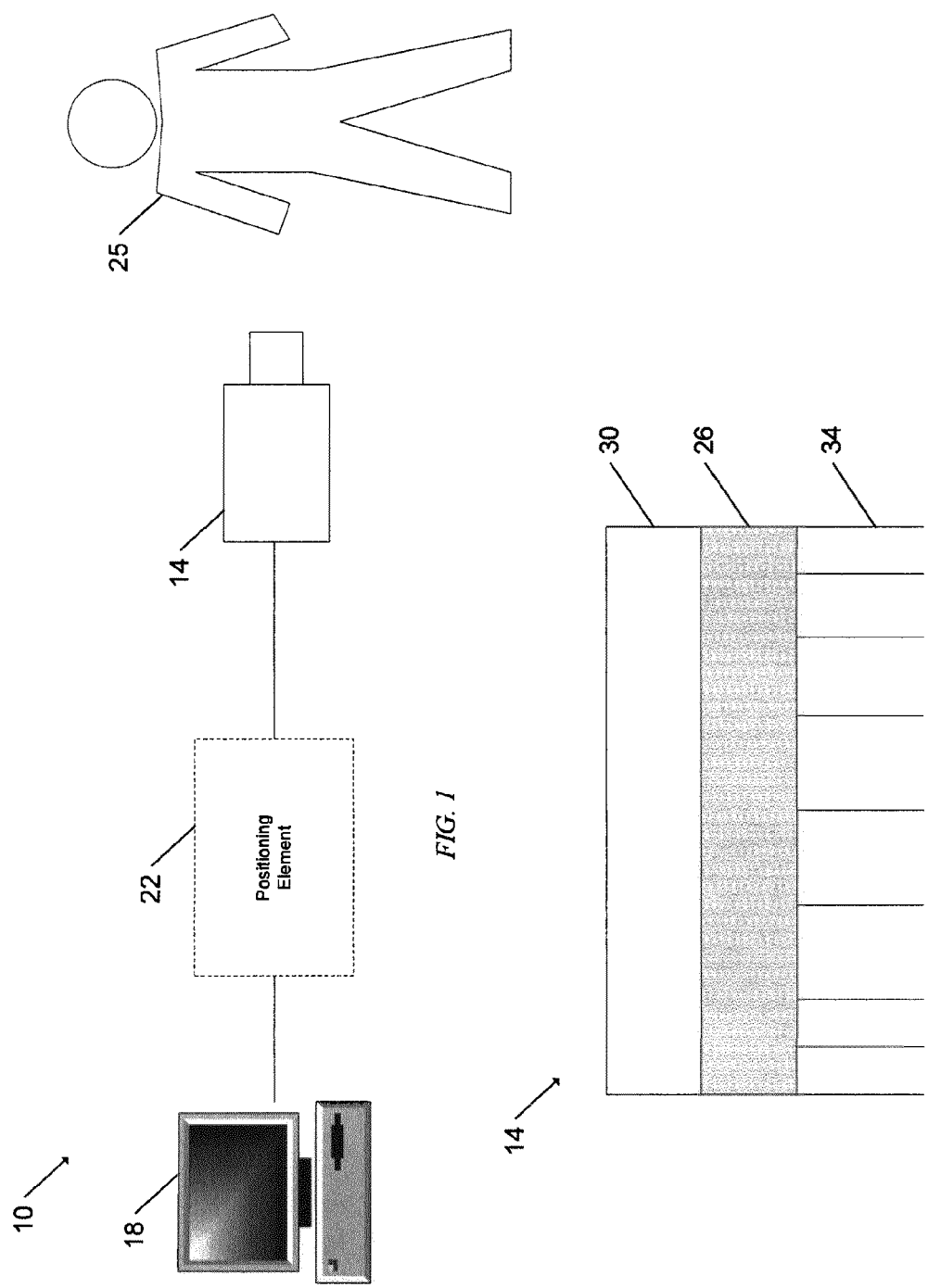

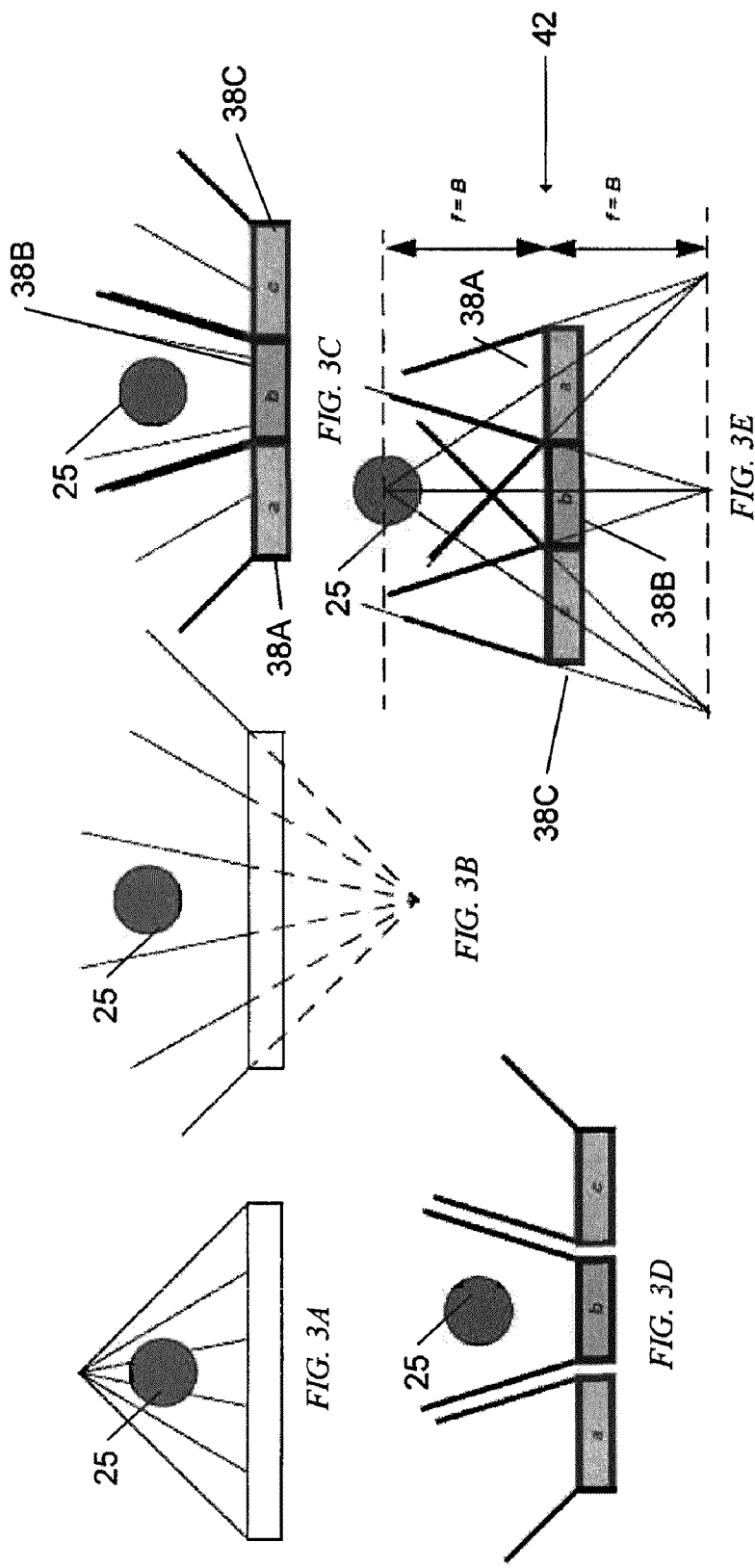

COLLIMATOR AND RELATED METHODS

TECHNICAL FIELD

The present subject matter relates to nuclear medicine. In more detail, it relates to systems, methods, and uses for a collimator.

BACKGROUND

Recently manufacturers have found a large market for dedicated cardiac single photo emission computed tomography (SPECT) systems. Small field-of-view (FOV) cardiac SPECT systems have become popular due to their compact design.

One company, Spectrum Digirad, developed dedicated cardiac SPECT systems that are small enough to be installed in a physician's office. These dedicated SPECT systems have relatively small gamma cameras, which are barely large enough to cover the heart. One feature of this system is that the detectors remain stationary and the projections are collected as the patient, sitting upright in a chair, is rotated.

Multi-pinhole collimation is the state-of-the-art in small animal SPECT, with the main advantage being the pinhole magnification effect, which allows a high-sensitivity, high-resolution image to be obtained. Taking advantage of modern large-area gamma cameras and multi-detector systems, the multi-pinhole technology is able to provide enough data for cardiac imaging without rotating the system gantry. A stationary system can take very fast snapshots, obtaining true dynamic imaging. The stationary system makes patient motion correction easier, and is less expensive to build and maintain.

SUMMARY

One problem faced in a stationary imaging system is the lack of sufficient view angles. In order to obtain more angular views, the pinholes are, in fact, operating in image reducing (instead of magnifying) mode. For a fixed pinhole aperture size, pinhole collimation provides acceptable detection sensitivity if the object is very small and placed very close to the pinhole; however, the detection sensitivity decreases dramatically if the object is moved away from the pinhole. As the object is moved farther into the image reduction zone, where the pinhole magnification factor is less than one, the pinhole detection sensitivity becomes worse.

In the above-referenced image reduction zone, the disclosed multi-divergent-beam collimator may become more sensitive than the pinhole for the same specified spatial resolution. As discussed in more detail below, one aspect of the disclosure relates to a multi-divergent-beam collimator. The collimator includes a plurality of inverted, ordered sections of a cone-beam collimator reassembled in a substantially reversed order relative to the ordering of the cone-beam collimator.

In some examples, the each of the sections has substantially similar dimensions. In other examples, the plurality of sections have dimensions different from others of the plurality of sections. Also, in some embodiments, a plurality of outer regions of the ordered regions have dimensions larger than a plurality of central regions.

In one example, the plurality of sections are portioned into a 3-by-3-by-3 array of ordered regions. In another example, the plurality of sections are portioned into a 2-by-3-by-2 array of ordered regions.

In another aspect, the disclosure is directed to a method of constructing a multi-divergent-beam collimator. The method can include partitioning a cone-beam collimator into a plurality of ordered regions, inverting the plurality of ordered regions, and reassembling in a substantially reversed order the inverted plurality of ordered regions.

In some examples, partitioning includes partitioning the cone-beam collimator into regions having substantially equal dimensions or sections having different dimensions. In some case, a plurality of outer regions of the ordered regions can have dimensions larger than a plurality of central regions.

In another aspect, the disclosure is directed to a SPECT system. Included in the system is a camera having a detector and a collimator. The collimator includes a plurality of inverted, ordered sections of a cone-beam collimator reassembled in a substantially reversed order relative to the ordering in the cone-beam collimator. The system also includes a computing system that receives measurements from the camera and processes those measurements.

In some examples, at least one of the camera, detector, and collimator are stationary. Of course, various combinations or more than one of the system elements can be stationary. For example, each of the elements can be stationary.

In some examples, the sections of the collimator have substantially similar dimensions. In other examples, the regions have different dimensions. For example, the a plurality of outer regions of the ordered regions can have dimensions larger than a plurality of central regions.

BRIEF DESCRIPTION OF THE DRAWINGS

The drawing figures depict one or more implementations in accord with the present teachings, by way of example only, not by way of limitation. In the figures, like reference numerals refer to the same or similar elements.

FIG. 1 is a block diagram of an embodiment of a SPECT system.

FIG. 2 is a simplified block diagram of an embodiment of a camera of a SPECT system.

FIG. 3A-3E are block diagrams depicting a one-dimensional representation of an embodiment of a method of making multi-divergent-beam collimator.

FIG. 4A-4B are block diagrams depicting ordered sections of a collimator and a reversal of that order.

FIG. 4C is a block diagram of an embodiment of a 3-by-3-by-3 multi-divergence-beam collimator.

FIG. 4D is a block diagram of an embodiment of a 2-by-3-by-2 multi-divergent-beam collimator.

DETAILED DESCRIPTION

Figure 5A:
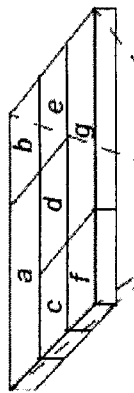
FIG. 5A-5D are block diagrams depicting a two-dimensional representation of an embodiment of a method of making the multi-divergent-beam collimator of FIG. 4D.

In the following detailed description, numerous specific details are set forth by way of examples in order to provide a thorough understanding of the relevant teachings. However, it should be apparent to those skilled in the art that the present teachings may be practiced without such details.

With reference to FIG. 1, a SPECT system 10 is shown and described. The system 10 includes a gamma camera 14 and a data processing computing system 18. In some examples, an optional positioning element 22 is included. The gamma camera 14 is in communication with the computing system 18.

In operation, the camera 14 acquires radioisotope gamma ray photons, which are emitted from portion of a body 25. The camera 14 converts the photons into electrical signals which represent that portion of the body emitting the photons.

As a result of the conversion, the electric signals are transformed into data indicative of photon energy. In essence, the camera captures one or more projection. The projections are fed into the computing system 18 for the purpose of reconstructing an image of a spatial distribution of a pharmaceutical substance that causes the emissions of the photons within the portion of the body by processing the data. The photon energy information is registered for the assessment of the amount of Compton scattering that is introduced in the acquisition. The reconstruction of an image of the portion of the body may be performed based on any appropriate existing algorithm. For example, the ML-EM algorithm and the OS-EM algorithm can be used. Further details of these algorithms can be found in: Lange A K and Carson R: EM reconstruction algorithms for emission and transmission tomography. *J. Comput. Assist. Tomogr.*, vol. 8, pp. 306-316, 1984; Hudson H M, Hutton B F, and Larkin R: Accelerated EM reconstruction using ordered subsets. *J. Nucl. Med.*, vol. 33, p. 960, 1991; and Hudson H M and Larki R S: Accelerated image reconstruction using ordered subsets of projection data. *IEEE Trans. Med. Imag.*, vol. 13, pp. 601-609, 1994, the entire contents of which are herein incorporated by reference.

With reference to FIG. 2 an example of a gamma camera 14 is shown and described. In some instances, the camera 14 includes a detector 26, a photo-multiplier 30, and collimator 34.

The detector 26 can be include at least one photon detector crystal facing the portion of the body 25. The photon detector crystal may be in the form of a semiconductor crystal or crystals. This crystal(s) may be selected from a first group including Cadmium-Telluride (CdTe), Cadmium-Zinc-Telluride (CeZnTe), Lead Iodine (PbI).

The photo-multiplier 30 is in communication with the detector 26. The photon detector crystal(s) in this case may be selected from a second group including Sodium Iodine (NaI), Bismuth Germanate (BGO), Yttrium Oxyorthosilicate (YSO), Cerium-doped Lutetium Oxyorthosilicate (LSO) and Cesium-Iodine (CsI) with solid state photo-diode or avalanche photo-diode (APD).

The detector crystals listed above have different characteristics that are relevant for SPECT imaging: they differ in their ability to resolve photon energy (also termed "energy resolution"), their internal spatial resolution and their stopping power. These characteristics affect the resolution and sensitivity of the resultant images. Therefore, SPECT cameras utilizing different detector crystals will yield different resolution, using the same reconstruction algorithm.

The detector 26, in some examples, may also be in the form of an array of photon detector crystals arranged in at least one row. The photon detector crystal array may be in the form of a plane or a ring surrounding the portion of the body. For example, detector 26 may be of the kind used in a known per se Anger camera.

The collimator 34 is in communication with the detector 26. The collimator is a device capable of collimating radiation. In some cases, the collimator includes a plurality of long narrow tube in which strongly absorbing or reflecting walls permit only radiation traveling parallel to the tube axis to traverse the entire length. Said another way, the collimator 34 is a device that filters a stream of gamma rays so that only those traveling parallel to a specified direction are allowed through.

In operation, camera 14 acquires radioisotope gamma ray photons, which are emitted from a portion the body 25. The photons pass through the collimator 34. The gamma photons impinge the photon detector crystal 26. If the crystal is a semiconductor crystal selected from the first group specified above, then the crystal converts the photons into electric signals, which are fed into the other components of the SPECT system 10 for processing. Alternatively, if the crystal is selected from the second group specified above, i.e. is of the kind that utilizing photo-multipliers, then the crystal converts photons into scintillation light, which is, thereafter, transformed into electric signals by photo-multiplier 30. These signals are processed by the computing system 18 to reconstruct an image of the portion of the body 26 of interest using know reconstruction algorithms.

As mentioned above, a stationary cardiac SPECT system is difficult to design and manufacture. An approach that might aid in achieving a truly stationary SPECT system maybe to design multi-divergent-beam collimator. In some applications, a multi-divergent-beam collimator SPECT system outperforms a multipinhole system in terms of image resolution and detection sensitivity. The performance can be characterized by the contrast-to-noise ratio, because the detection sensitivity is inversely related to the image noise. Using a multi-divergent-beam collimator can produce a sufficient number of angular views that reconstruction of the image is possible without, in some instances, having to rotate the camera 14. Further, in cases where the camera 14 is positioned, the number of positions required to capture photon emissions from the body 26 is reduced. There are numerous approaches to designing a multi-divergent-beam collimator. One approach is to design each divergent zone independently which usually results in a very expensive fabrication cost. A more economical solution is now discussed.

With reference to FIG. 3A-FIG. 3D, a method of constructing a multi-divergent-beam collimator is shown and described. In FIG. 3A-FIG. 3D, a one-dimensional example is discussed. In FIG. 3A, a cone-beam collimator is constructed. In FIG. 3B, the cone-beam collimator is inverted (e.g., flipped upside down) and becomes a divergent-beam collimator. In FIG. 3C, the divergent-beam collimator is portioned into sections 38A, 38B, 38C (generally sections 38). The sections 38 are assigned an order. In FIG. 3D, the ordered sections 38 are separated. In FIG. 3E, the ordered section 38 are reassembled (e.g., glued together) in the reverse order. As shown, the resulting multi-divergent-beam collimator produces multiple angular views of the portion of the body 26 of interest.

When designing the multi-divergent-beam collimator 42, the original convergent-beam collimator is assumed to have a focal-length f, then such a converted multi-divergent-beam collimator 42 will have a common field-of-view that has a distance f away from the center of the collimator. In other words, one way to design a multi-divergent-beam collimator 42 with the center of the region of interest at a distance B from the collimator, first fabricate a convergent-beam collimator that has a focal-length B, then cut, rearrange, and glue the sections to construct a multi-divergent-beam collimator 42.

Figures 4A, 4B, 4C, 4D:
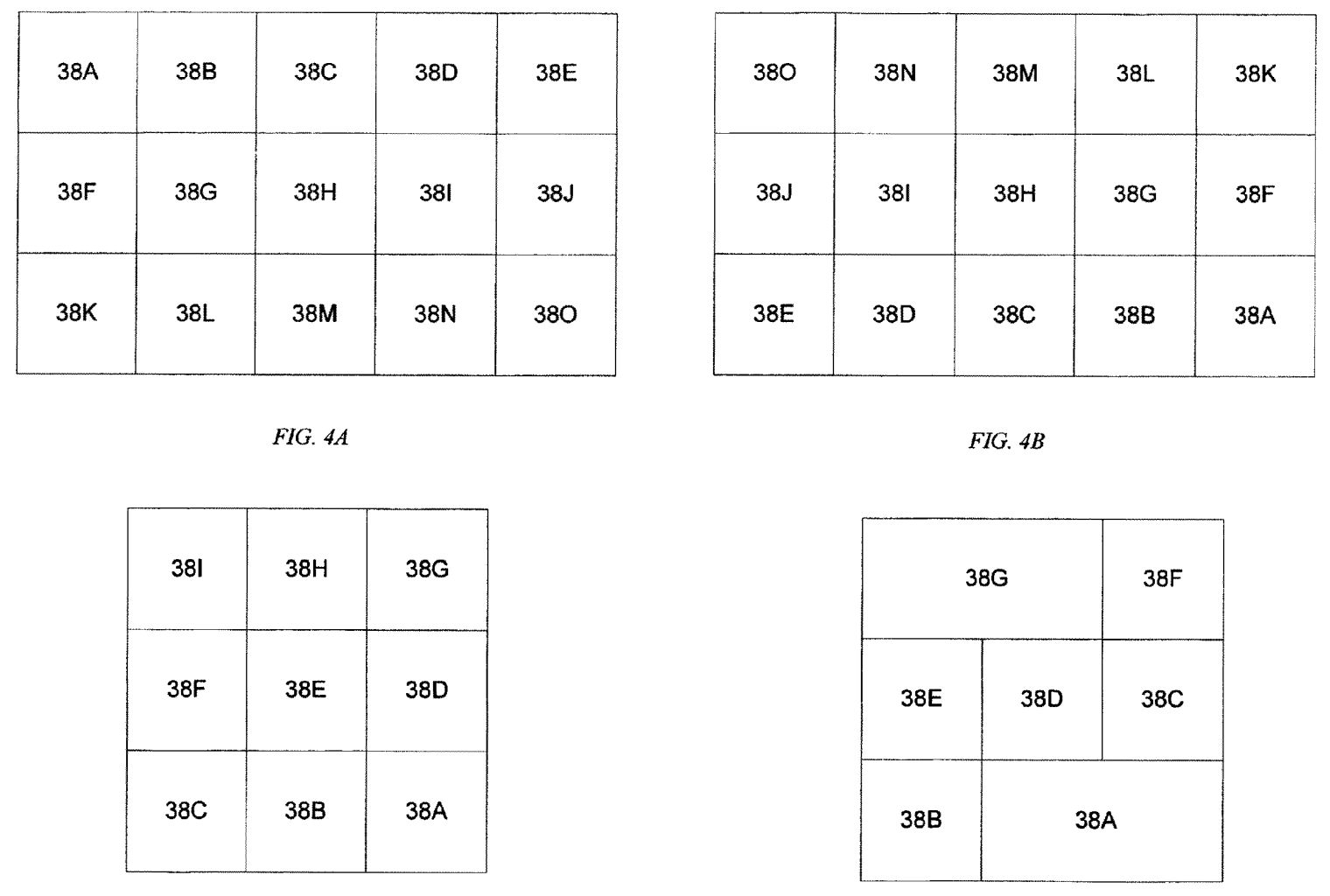

In more detail and with reference to FIG. 4A and FIG. 4B, sections 38 are fabricated and then reassembled in reversed order. In this example, assume that the collimator has a frame of approximately 53 cm by 38 cm. The cone-beam focal length is approximately 400 mm. The hexagonal hole diameter is 1.9 mm. The septa are 0.23 mm. The core thickness is 35 mm. The collimator has a resolution at 100 mm is approximately 8.1 mm. The sensitivity of the collimator when operating in parallel mode is 334. The septa penetration at 140 keV is 0.6%. Working of these assumption, the cone-beam collimator is constructed as in FIG. 3A. Again, the cone-beam collimator is flipped upside down (e.g., inverted).

In FIG. 4A, the inverted collimator is portioned into sections 38. As shown, the collimator is portioned into fifteen sections 38 having substantially similar dimensions. Of course, the sections can have different dimensions as will be described in more detail below. As shown, the sections 38 have a square shape. However, other shapes can be used. For example, the sections 38 can be rectangular, triangular, or some other polygonal shape. Of course, combinations of shapes an also be used. For example, a combination of squares and rectangles can be employed. As shown in FIG. 4A, the sections 38 are assigned an order. As shown, the sections 38 are labeled 38A-38O in a horizontal manner (e.g., from right to left across a row). Of course, other orderings can be used (e.g., vertical assignments). After assigning the order, the sections 38 are cut and then rearranged and reassembled in reverse order as shown in FIG. 4B. That is, section 38O that was previously in the bottom right hand corner is now positioned in the upper left hand corner.

With reference to FIG. 4C a 3-by-3-by-3 collimator is shown. Again, the sections 38 can have various shapes and sizes. The section 38 parameters of the collimator 42 depends on the detector size 26 and the trade-off between detection resolution and angular sampling. For a given detector size 26, the use of more view-angles correlates with more partitioned zones, which results in smaller projection images. The system 10 resolution in SPECT is dominated by the collimator and the distance between the portion of the body of interest and the collimator. Due to poor sensitivity of SPECT, the image on the detector 26 cannot be too small. Assume in FIG. 4C that SPECT scanner detectors are 53 cm in the transaxial direction. Considering the dead area around the partitioned collimator zones, it is practical to have three zones in both the transaxial and the axial directions, resulting in a partition similar to that of the 3-by-3-by-3 multi-pinhole partition.

In FIG. 4D a 2-by-3-by-2 multi-divergent-beam collimator is shown and described. This configuration provides additional view angles when compared to the 3-by-3-by-3 configuration of FIG. 4C.

A method of constructing a multi-divergent-beam collimator 42 having a 2-by-3-by-2 configuration is shown and described with reference to FIG. 5A-5D. When compared to FIG. 3A-FIG. 3E, a substantially similar process is followed. FIG. 5A-5D show a two-dimensional example. In this configuration, the top and bottom rows of the collimator 42 include two sections 38. The middle row includes three sections 38.

Figure 6B:
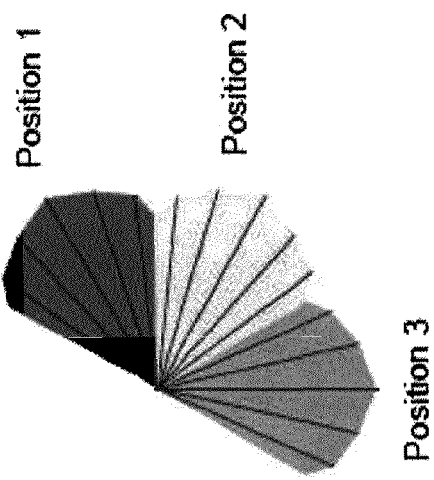
FIG. 6B is a block diagram depicting the view angles of the top row of the collimator of FIG. 4D.
Figure 6A:
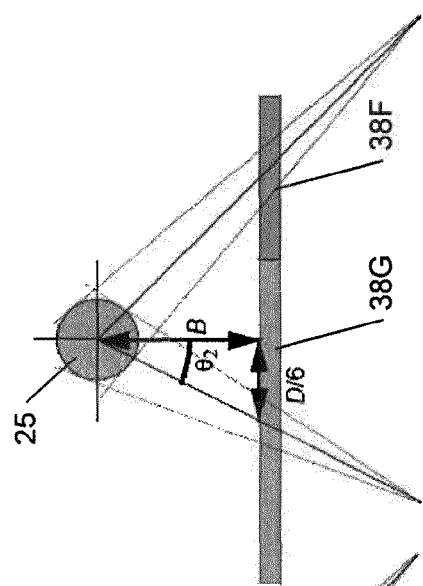
FIG. 6A is a block diagram depicting the view angles of the middle row of the collimator of FIG. 4D.
Figure 6D:
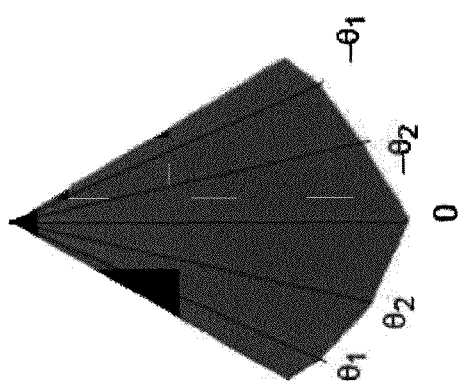
FIG. 6D is a depiction of showing how an embodiment of the collimator of FIG. 4D can cover the 180° view angle.
Figure 6C:
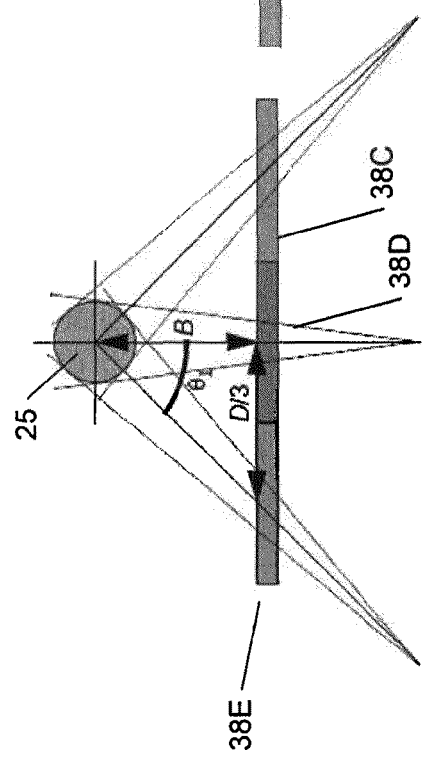
FIG. 6C is a depiction of a relative view angles of the collimator of FIG. 4D.

With reference to FIG. 6A and FIG. 6B, the additional view angles provided by the 2-by-3-by-2 configuration of FIG. 4D is shown and described. The middle row of divergent-beam collimators 42 has three zones that provide view-angles of $\theta_1$, 0, and $-\theta_1$ relative to the collimator's normal direction as in FIG. 6A, where $\theta_1$ is calculated as $\theta_1 = a\tan^{-1}(D/(3B))$. The top row has two zones and provides view angles of $\theta_2$ and $-\theta_1$, where $\theta_2$ is given as $\theta_2 = a\tan^{-1}(D/(6B))$, as shown in FIG. 6B. Similarly, the bottom row provides view angles of $\theta_1$ and $-\theta_2$. The shown 2-by-3-by-2 configuration of the sections 38 provides view angles: $\theta_1, \theta_2, 0, -\theta_2, -\theta_1$, as shown in FIG. 6C. Note that at $\pm\theta_1$ the data are measure twice, but at different axial view angles.

In one example, assume that D=53 cm and B=40 cm. Using this assumption, $\theta_1 = 24°$ and $\theta_2 = 12.5°$. Thus $\theta_1$ is almost twice as large as $\theta_2$. The view angles are substantially uniformly sampled. Assuming that three detectors are used with an angle of 60.5° between them, than an angular range over 181.5° is substantially uniformly covered as shown in FIG. 6D. For a short distance B, the angular coverage is larger. For example, assume that D=53 cm and B=30 cm, then $\theta_1 = 30.5°$, $\theta_2 = 16.40°$, and the angular coverage with three detector positions is substantially 232.2°. If D=53 cm and B=25 cm, then $\theta_1 = 35.2°$, $\theta_2 = 19.5°$, and the angular coverage with three detector positions is substantially 269.7°. If two detector positions are used, the angular coverage is 179.8°. That is, if the distance B can be shortened to 25 cm, it may be possible to use two detector positions for cardiac SPECT imaging with the multi-divergent-beam collimator 42.

The most substantial problem faced in a stationary imaging system is the lack of sufficient view angles. In order to obtain more angular views, the pinholes are, in fact, operating in image reducing (instead of magnifying) mode. For a fixed pinhole aperture size, pinhole collimation provides excellent detection sensitivity if the object is very small and placed very close to the pinhole; however, the detection sensitivity decreases dramatically if the object is moved away from the pinhole. As the object is moved farther into the image reduction zone, where the pinhole magnification factor is less than 1, the pinhole detection sensitivity becomes worse. In this zone, the divergent-beam collimator becomes more sensitive than the pinhole for the same specified spatial resolution. For both pinhole and divergent-beam systems, the imaging system's field-of-view (FOV) is determined by the detector size and the object-to-image reduction factor. If the detectors are the same and the image reduction factors are the same, both systems have the same FOV.

In a SPECT study, the organ of interest is always assumed to be in the field-of-view (FOV) of the gamma camera; the background and other organs may be truncated, or not in the FOV, thus they are not measured. Dedicated systems are usually small, and data truncation happens frequently. A potential drawback of the stationary SPECT system is the lack of a sufficient number of views. To solve this problem, the pinhole imaging system is used, operating in image reduction mode, so that many angular views of the object can be obtained at a single detector position. In order for all pinholes to see the heart, the patient must be positioned away from the collimator, although this setup reduces the resolution and detection sensitivity.

Figure 7:
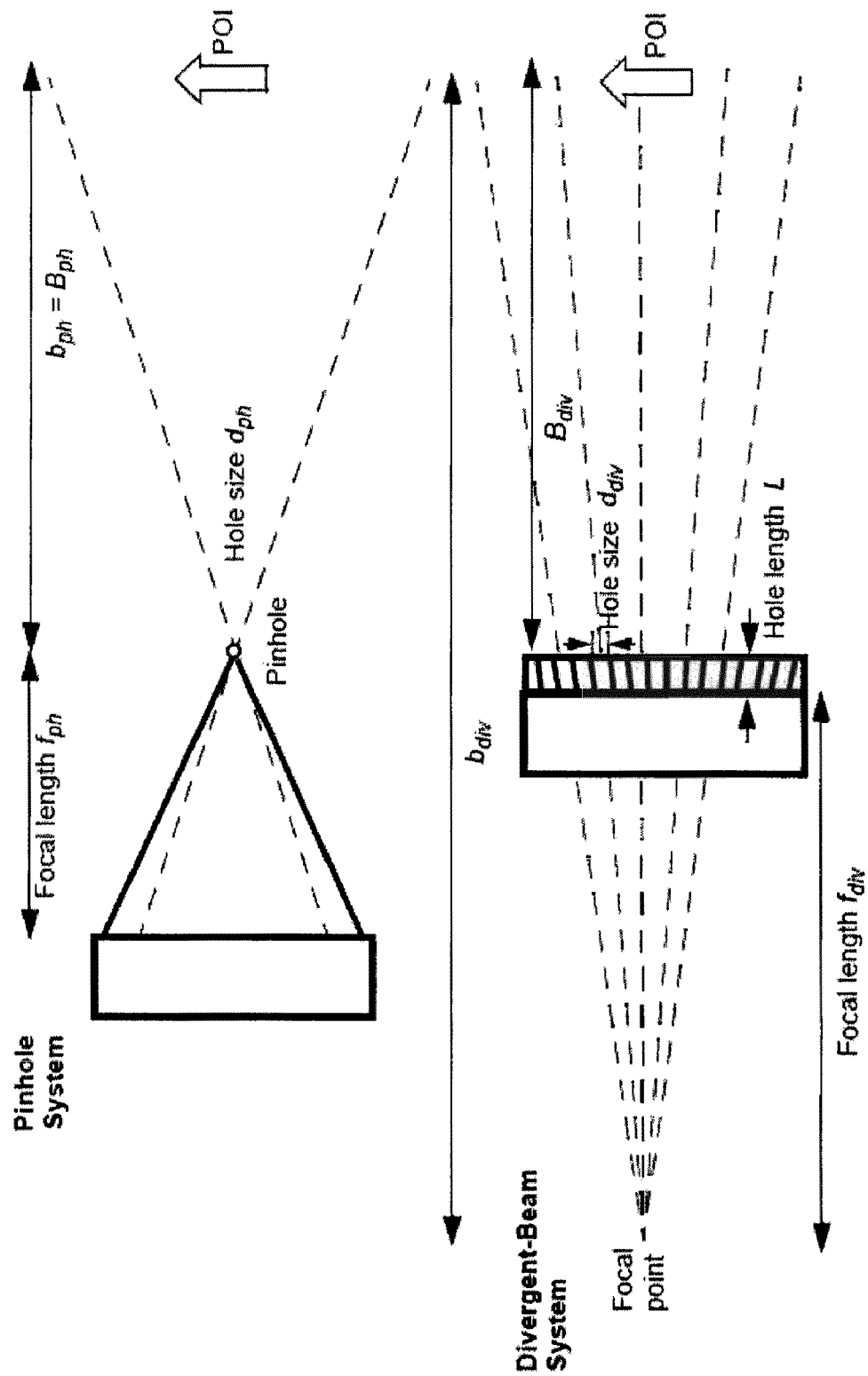
FIG. 7 depicts parameters in pinhole and divergent-beam systems used in some embodiments described herein.

FIG. 7 illustrates a pinhole collimator and a divergent-beam collimator. Here the assumption is made that the pinhole system has a focal-length $f_{ph}$ and distance $b_{ph}$ from the focal point to the point-of-interest (POI). Similarly, the divergent-beam system has a focal-length $f_{div}$ and distance $b_{div}$ from the focal point to the point-of-interest (POI). For a fair comparison, these two systems are required to have the same image reduction factor $$f_{ph}/b_{ph} = f_{div}/b_{div}, \quad (1)$$

and that the object is the same distance $$B_{ph} = B_{div} \text{ (that is, } b_{ph} = b_{div} - f_{div} - L) \quad (2)$$

away from the collimator.

In order to compare these two systems, a small object is placed at the POI and required that the systems give identical spatial resolutions on the detectors. Since the resolution of the two systems is fixed, the superior system provides greater geometric detection efficiency. These two systems are required to give identical detection sensitivities on the detectors. Because the sensitivity of the two systems is fixed, the superior system will provide better resolution. Larger detection sensitivity means that more gamma photons can be detected, and this results in lower Poisson noise in the data. Better resolution means smaller objects (e.g., lesions) can be resolved. The POI is further assumed to be on the central axis of the pinhole.

For the pinhole geometry, there are the following two relations:

$$\text{Resolution: } R_{ph} \approx d_{ph} \frac{f_{ph} + b_{ph}}{f_{ph}} \quad (3)$$

$$\text{Geometric Efficiency: } g_{ph} \approx \frac{d_{ph}^2}{16 b_{ph}^2}. \quad (4)$$

For the divergent-beam geometry, there are the following relations:

$$\text{Resolution: } R_{div} \approx d_{div} \frac{b_{div} - f_{div}}{L} \left(1 + \frac{1}{2} \frac{L}{f_{div}}\right) \quad (5)$$

$$\text{Geometric Efficiency: } g_{div} \approx K^2 \left(\frac{d_{div}}{L}\right)^2 \left(\frac{f_{div} + L}{b_{div}}\right)^2 \quad (6)$$

where the septal thickness t is ignored for a moment, otherwise there is a $$\left(\frac{d_{div}}{d_{div} + t}\right)^2$$

factor in $g_{div}$.

The requirement for the two systems having the identical spatial resolution on the detectors implies $$R_{ph} = R_{div}, \quad (7)$$

and from (3), (5) and (7), we have $$d_{ph} \frac{f_{ph} + b_{ph}}{f_{ph}} = d_{div} \frac{b_{div} - f_{div}}{L} \left(1 + \frac{L}{2 f_{div}}\right). \quad (8)$$

In order to satisfy (8) and (1) the hole-length L of the divergent-beam collimator must satisfy $$L = \frac{f_{div}}{\left(\beta \cdot \frac{b_{div} + f_{div}}{b_{div} - f_{div}} - \frac{1}{2}\right)} \quad (9)$$

[We denote this $L$ as $L_R$]

where $\beta = \frac{d_{ph}}{d_{div}}$.

After the resolution is specified, equations (4) and (6) can be used to compare their detection sensitivities as $$\frac{g_{div}}{g_{ph}} = \frac{K^2 \left(\frac{d_{div}}{L}\right)^2 \left(\frac{f_{div} + L}{b_{div}}\right)^2}{\frac{d_{ph}^2}{16 b_{ph}^2}} \quad (10)$$

where K is a constant that depends on the hole shape (~0.24 for round holes and ~0.26 for hexagonal holes). If we assume K=0.25 then $$\frac{g_{div}}{g_{ph}} = \frac{\left(\frac{d_{div}}{L}\right)^2 \left(\frac{f_{div} + L}{b_{div}}\right)^2}{\frac{d_{ph}^2}{b_{ph}^2}} \quad (11)$$

$$= \left[\frac{1}{\beta} \cdot \frac{b_{ph}(f_{div} + L)}{b_{div} L}\right]^2.$$

Pinhole and divergent-beam collimators with the same image reducing factor can have different performances in terms of resolution. When the divergent-beam collimator hole-length L satisfies (9), both collimators give the same spatial resolution on the detectors for an object at the POI. If $$L > L_R \quad (12)$$

the divergent-beam collimator will provide better resolution than the pinhole. Furthermore, if $$L < L_R \quad (13)$$

the pinhole collimator will provide better resolution than the divergent-beam collimator.

The requirement that the two systems have identical detection sensitivities on the detectors implies $$g_{ph} = g_{div}. \quad (14)$$

From (11) and (2), (14) becomes $$\frac{b_{ph}(f_{div} + L)}{\beta b_{div} L} = 1 \text{ or } \frac{(b_{div} - f_{div} - L)(f_{div} + L)}{\beta b_{div} L} \quad (15)$$

$$= 1.$$

Solving for L from Eq. (15), results $$L = \frac{-(2 f_{div} + \beta b_{div} - b_{div}) + \sqrt{(2 f_{div} + \beta b_{div} - b_{div})^2 + 4 f_{div}(b_{div} - f_{div})}}{2} \quad (16)$$

[We denote this $L$ as $L_S$].

After the sensitivity is specified, equations (1), (3) and (5) can be used to compare the resolution as $$\frac{R_{div}}{R_{ph}} = \frac{f_{ph}}{\beta \cdot L} \cdot \frac{b_{div} - f_{div}}{f_{ph} + b_{ph}} \cdot \left(1 + \frac{1}{2}\frac{L}{f_{div}}\right) \quad (17)$$

$$= \frac{1}{\beta} \cdot \frac{b_{div} - f_{div}}{b_{div} + f_{div}} \cdot \left(\frac{f_{div}}{L} + \frac{1}{2}\right).$$

Pinhole and divergent-beam collimators with the same reduction factor can have different performances in terms of detection sensitivity. When (15) is satisfied, both collimators give the same sensitivity for an object at the POI. If $$L < L_S \quad (18)$$

the divergent-beam collimator will provide better sensitivity than the pinhole. Additionally, if $$L > L_S \quad (19)$$

the pinhole collimator will provide better sensitivity than the divergent-beam.

Consequently, if L is chosen in the range of LR<L<LS, the divergent-beam system will outperform the pinhole system in both resolution and sensitivity. It can be established that 0<LR<LS is the case in some embodiments described herein, and that some embodiments can always be designed to have a divergent-beam imaging geometry that outperforms the pinhole system in both resolution and sensitivity.

The above conclusion is true when the pinhole system is operating in the image reducing mode. If the pinhole system is operating in the image magnifying mode (as widely used in small animal imaging), the counterpart of the divergent-beam system is the cone-beam system.

For any positive values of $f_{div}$ and $b_{div}$ with $b_{div} > f_{div} > 0$, and for practical values of $\beta > 2$, we have $$b_{div} + f_{div} > \frac{b_{div}}{2\beta} > \frac{b_{div} - f_{div}}{2\beta}, \quad (20)$$

i.e., $\beta \cdot \frac{b_{div} + f_{div}}{b_{div} - f_{div}} - \frac{1}{2} > 0.$ From (9), $$L_R = \frac{f_{div}}{\left(\beta \cdot \frac{b_{div} + f_{div}}{b_{div} - f_{div}} - \frac{1}{2}\right)} > 0. \quad (21)$$

Here the assumption of $\beta = d_{ph}/d_{div} > 2$ is true, because a typical value of $d_{ph}$ is approximately 6 mm and the typical $d_{div}$ for an LEHR (low energy high resolution) collimator is about 1.1 mm and for an LEHS (low energy high sensitivity) collimator about 2.54 mm. This gives a typical β value of 2.36~5.45, which is greater than 2.

Now we will show LS>LR, that is, $$\frac{-(2f_{div} + \beta b_{div} - b_{div}) + \sqrt{(2f_{div} + \beta b_{div} - b_{div})^2 + 4f_{div}(b_{div} - f_{div})}}{2} > \frac{f_{div}}{\beta \cdot \frac{b_{div} + f_{div}}{b_{div} - f_{div}} - \frac{1}{2}}, \quad (22)$$

or equivalently $$\left(\frac{2f_{div}}{\beta \cdot \frac{b_{div} + f_{div}}{b_{div} - f_{div}} - \frac{1}{2}}\right)^2 + \quad (23)$$

$$2(2f_{div} + \beta b_{div} - b_{div})\left(\frac{2f_{div}}{\beta \cdot \frac{b_{div} + f_{div}}{b_{div} - f_{div}} - \frac{1}{2}}\right) - 4f_{div}(b_{div} - f_{div}) < 0$$

which can be simplified as $$(-4\beta^2 + 6\beta)f_{div}b_{div} + (-4\beta^2 + 4\beta - 1)f_{div}^2 - (2\beta - 1)b_{div}^2 < 0. \quad (24)$$

Since $f_{div} < b_{div}$, if β>1.5 the left-hand-side of (23) is upper bounded by $$(-4\beta^2 + 6\beta)f_{div}^2 + (-4\beta^2 + 4\beta - 1)f_{div}^2(2\beta - 1)f_{div}^2 = -4f_{div}^2\beta(\beta - 2) \quad (25)$$

When β>2, the expression in (24) is negative. In other words, when β>2, LS>LR. A practical value of β is in the range of 2.36~5.45. Therefore, in some embodiments described herein LS>LR in all cases.

The relationship 0<LR<LS assures the existence of divergent-beam collimators that are superior to the image-reducing mode pinhole collimator in terms of both resolution and detection sensitivity.

Hereafter we address more realistic collimation situations where we consider collimator penetration and a distributed source, which may not be exactly at the center of the field-of-view. We assume that the radiation source is a three-dimensional cube of size 15 cm×15 cm×15 cm containing the heart, the collimator is made of lead, and there is an angle θ between a general emission ray and the central line of the collimator. Based on these generalizations, equations (3)-(6) are revised as (26)-(29):

$$\text{Pinhole Collimator Resolution: } R_{ph} \approx \hat{d}_{ph}\frac{f_{ph} + b_{ph}}{f_{ph}} \quad (26)$$

$$\text{Geometric Efficiency: } g_{ph} \approx \frac{\hat{d}_{ph}^2 \cos^3\theta}{16 b_{ph}^2} \quad (27)$$

where $\hat{d}_{ph} = \sqrt{d_{ph}[d_{ph} + 2\mu^- \tan(\alpha/2)]}$ is Anger's effective pinhole diameter, μ is the linear attenuation coefficient of the collimator material, and α is the pinhole acceptance angle. More accurate effective pinhole diameters can consider photon penetration. For large pinholes (with a diameter larger than 1 mm), Anger's effective pinhole diameter is acceptable, and will be adopted and incorporated herein for its simplicity. Similarly, for the divergent-beam geometry, we have:

$$\text{Divergent-Beam Collimator Resolution: } R_{div} \approx \quad (28)$$

$$d_{div}\frac{b_{div} - f_{div}}{\hat{L}} \cdot \frac{1}{\cos\theta}\left(1 + \frac{1}{2}\frac{\hat{L}}{f_{div}}\right)$$

$$\text{Divergent-Beam Collimator Geometric Efficiency: } g_{div} \approx \quad (29)$$

$$K^2\left(\frac{d_{div}}{\hat{L}}\right)^2\left(\frac{d_{div}}{d_{div} + t}\right)^2\left(\frac{f_{div} + L}{b_{div}}\right)^2$$

where t is the septal thickness and $\hat{L} = (L - 2\mu^{-1})/\cos\theta$ is the effective hole-length, and K=0.26 for a hexagonal collimator hole.

For a stationary system, one concern is the lack of sufficient view angles. Both the multi-pinhole and multi-divergent-beam systems can provide additional view angles at a fixed detector position. The additional view angles provided by these two types of systems are different. We will use the 1D version to illustrate the basic principle.

Figure 8A:
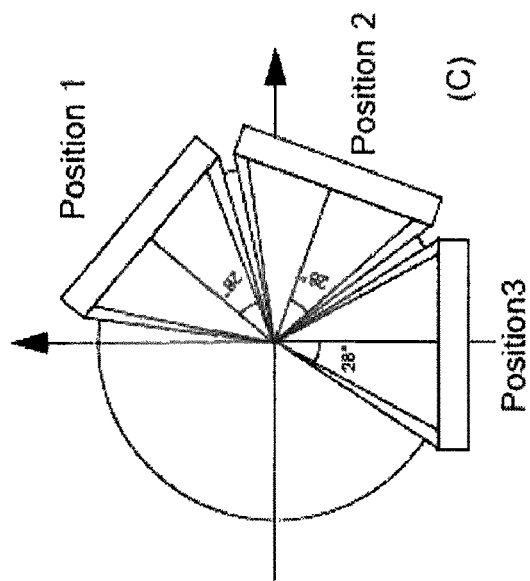
FIGS. 8A-8C depict additional view-angles that are created by multi-pinhole and multi-divergent beam systems, illustrating, in FIG. 8C that if a multi-divergent beam system is positioned in 3 non-overlapping locations, it can cover over 180° of view-angles.

The multi-pinhole geometry is shown in FIG. 8A, where the angle $\theta_{ph}$ is the additional view-angle a multi-pinhole system provides. The maximum value of the additional view-angle can be determined by $$\theta_{ph}^{max} = \tan^{-1} \frac{\frac{D}{2} - \frac{pf_{ph}}{B_{ph}}}{f_{ph} + B_{ph}} \quad (30)$$

where D is the detector size and ρ is the radius of the object of interest.

Figure 8B:
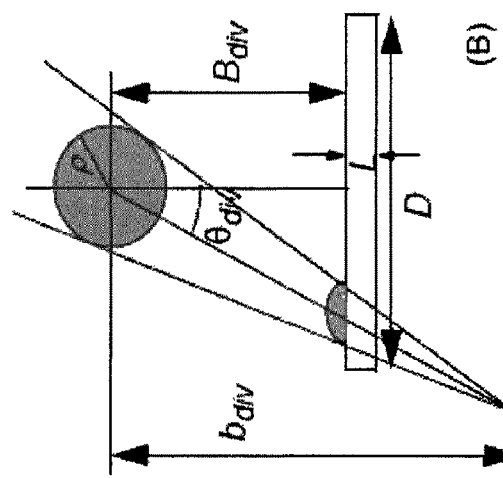

The multi-divergent-beam geometry is shown in FIG. 8B, where the angle $\theta_{div}$ is the additional view-angle provided by the multi-divergent-beam system. The maximum value of the additional view-angle can be determined by $$\theta_{div}^{max} = \tan^{-1} \frac{\frac{D}{2} - \frac{\rho(b_{div} - B_{div} - L)}{b_{div}}}{B_{div} + L}. \quad (31)$$

As a special case, in some embodiments described herein, $b_{div} = 2B_{div}$, then (31) becomes $$\theta_{div}^{max} = \tan^{-1} \frac{D - \rho + \frac{\rho L}{B_{div}}}{2(B_{div} + L)}. \quad (32)$$

Figure 8C:
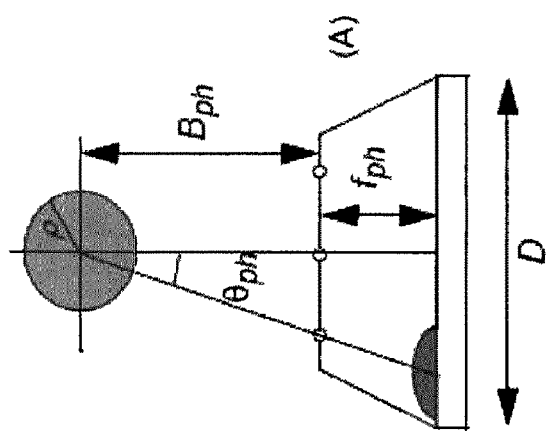

For given numerical values, the maximum value of the additional view-angle provided by the pinhole is less than the maximum value of the additional view-angle provided by the multi-divergent-beam system, and each detector position using the multidivergent-beam collimator can cover approximately 60° of view angles. Therefore, three detector positions can acquire projections over 180° as shown in FIG. 8C. On the other hand, for the multi-pinhole system, three detector positions are less likely to cover 180°.

This analysis shows a distinct advantage of the multi-divergent-beam collimator over the multi-pinhole collimator: The multi-divergent-beam collimator can provide a larger view-angle range than the multi-pinhole collimator. This analysis can be readily extended to practical 2D multi-pinhole and multi-divergent-beam collimators. The view-angle range in the axial direction is also larger for the multi-divergent-beam collimator than for the pinhole collimator.

Under the assumption that the image reducing factor $f_{div}/b_{div}$ in (1) is 0.5, $f_{div}=40$ cm and β=4, the value of LR from (9) is $L_R = 2f_{div}/(6\beta - 1) = 3.48$ cm.

At L=LR=3.48 cm the sensitivity gain given by (11) is $g_{div}/g_{ph}=2.03$. This implies that when the pinhole and the divergent-beam systems have the same spatial resolution at the center of the object, the divergent-beam system has a 2-fold sensitivity gain over the pinhole system.

In some embodiments, under the assumption that the image systems satisfy assumption (2), the value of $L_S$ can be directly solved from (16) as $L_S=4.92$ cm. That is, when the collimator hole-length is chosen as $L_S=4.92$ cm, both systems have the same sensitivity at the center of the object, while the divergent-beam system has better resolution than the pinhole system, with a resolution ratio $R_{div}/R_{ph}=0.72$. In this numerical example, $L_S=4.92$ cm is rather long from a practical point of view. Thus, for a practical hole length L, the divergent-beam collimator will have better sensitivity than the pinhole.

Figure 11B:
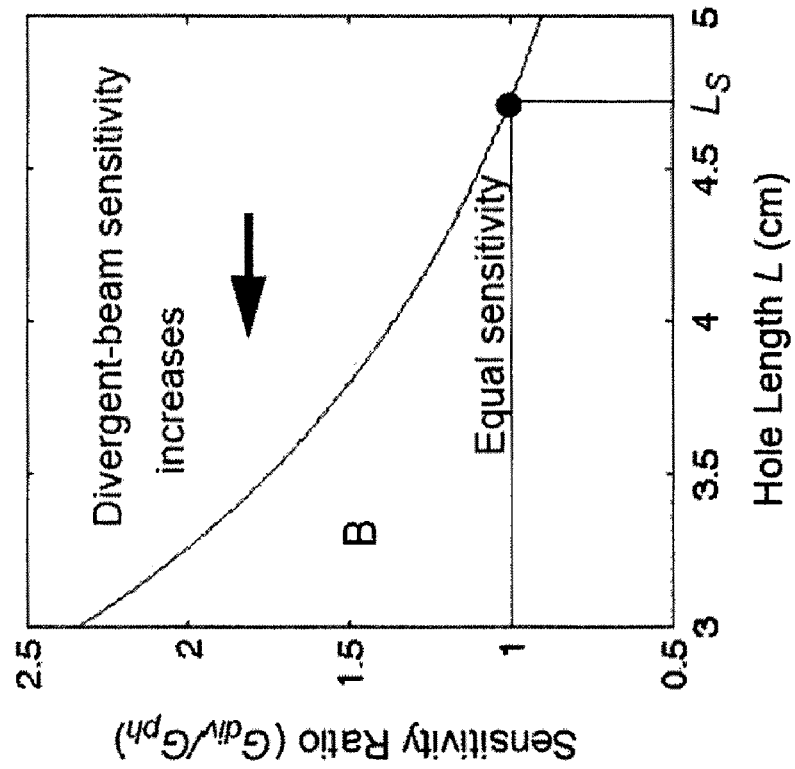
FIGS. 11A-11B depict graphs that compare resolution and sensitivity of a divergent-beam collimator and a pinhole collimator.
Figure 11A:
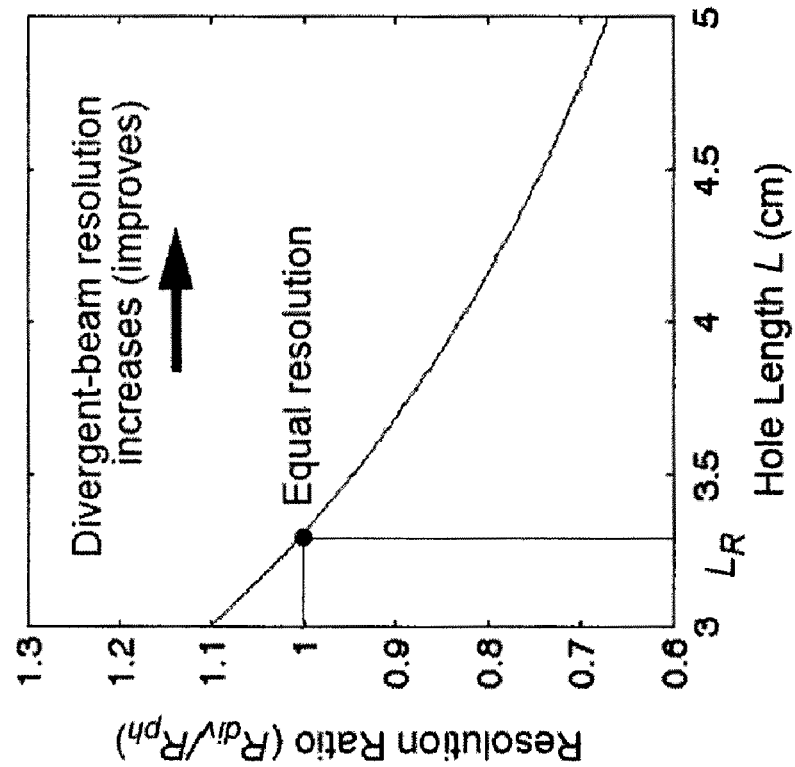

We now compare the divergent-beam collimator and the pinhole collimator based on the two assumptions expressed in Eqs. (1) and (2), and that the two collimators have the same reduction factor (0.5) and the same distance (40 cm) from the center of the object to the collimator. These two requirements result in $f_{div}=40$ cm, $b_{div}=80$ cm, $f_{ph}=20$ cm, and $b_{ph}=40$ cm. The pinhole diameter is $d_{ph}=6$ mm, α=90°, the divergent collimator hexagonal hole size is $d_{div}=1.5$ mm, and the septal thickness is 0.23 mm. If we assume the hole size of 1.5 mm, hole length of 3.6 cm, the linear attenuation coefficient of lead at 140 keV of 21.66 per cm, then the penetration percentage is less than 6%. Using (26)-(29), a divergent-beam to pinhole resolution ratio plot and a sensitivity ratio plot is illustrated in FIGS. 11A-11B. From the curves, we have the equal resolution parameter $L_R=3.3$ cm and at this hole-length the divergent to pinhole sensitivity gain is 2. From the sensitivity ratio plot, the equal sensitivity hole-length LS=4.7 cm and at this hole-length the divergent to pinhole resolution FWHM reduction factor is 0.7.

For a multi-pinhole system setup: D=53 cm, ρ=10 cm, $B_{ph}=40$ cm, and $f_{ph}=20$ cm, the maximum value of the additional view-angle (for pinhole) is=19.7° according to (30).

For an equivalent multi-divergent-beam system setup: D=53 cm, ρ=10 cm, L=3.48 cm and $B_{div}=B_{ph}=40$ cm, the maximum value of the additional view-angle (for divergent system) is=26.8° according to (32). Thus at a fixed detector position, the multi-divergent-beam system can provide a larger angular range than the multi-pinhole system.

Figures 9A, 9B:
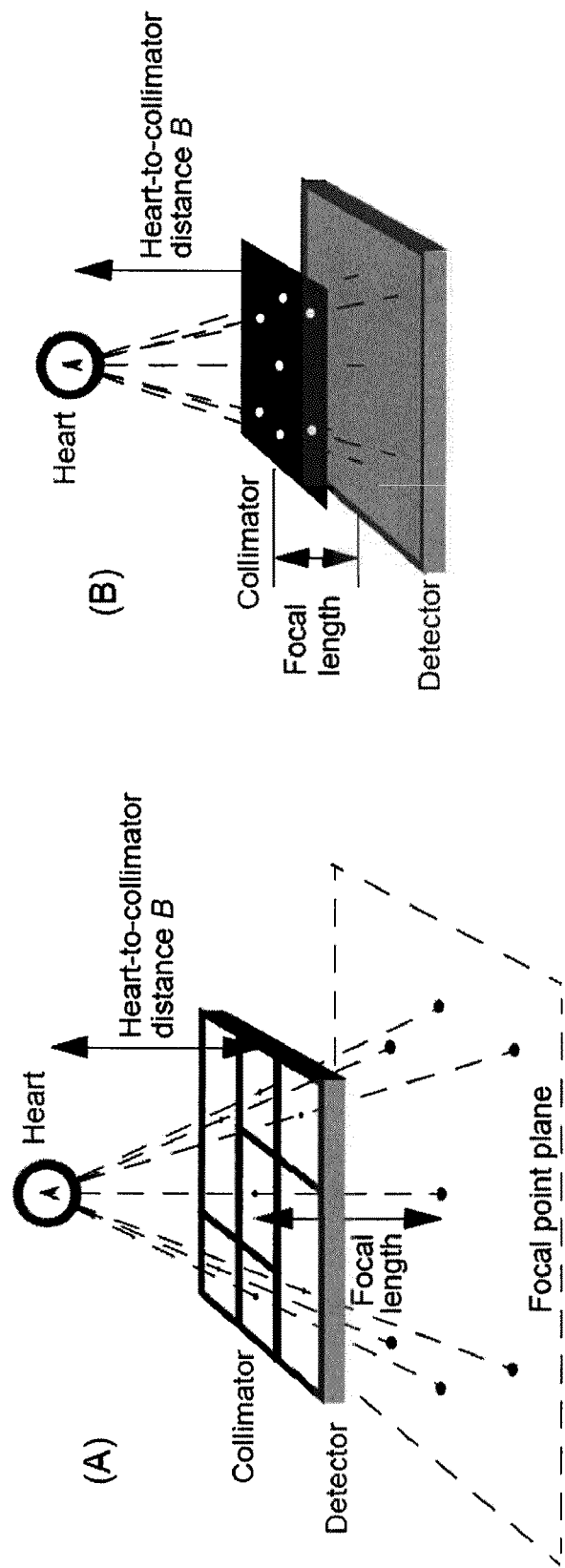
FIGS. 9A-9B depict simulation set-ups for both the multi-divergent beam system (FIG. 9A) and the multi-pinhole system (FIG. 9B).

Two comparison studies compare the multi-divergent-beam and multi-pinhole imaging systems via computer simulations. In both systems, the collimators had the same 2-3-2 partitions as shown in FIGS. 9A-9B. Each detector position provided 5 view-angles in the transaxial direction. Each sub-detector zone was a 64×64 matrix with a pixel size of 1.25 mm. Three detector positions were used. Both collimators had the same image reduction factor of 0.5. The adjacent detectors were positioned 60° apart. The cardiac phantom had an outside radius of 6 cm and an inner radius of 5 cm. The heart-to-collimator distance was 40 cm. In projection data generation, we assumed that these two systems had the same spatial resolution at the center of the object, which led to a 2-fold sensitivity gain for the multi-divergent-beam system over the multi-pinhole system. The iterative ML-EM algorithm was used to reconstruct the images with 5 iterations. No resolution compensation was used in image reconstruction.

Figures 10A, 10B, 10C, 10D:
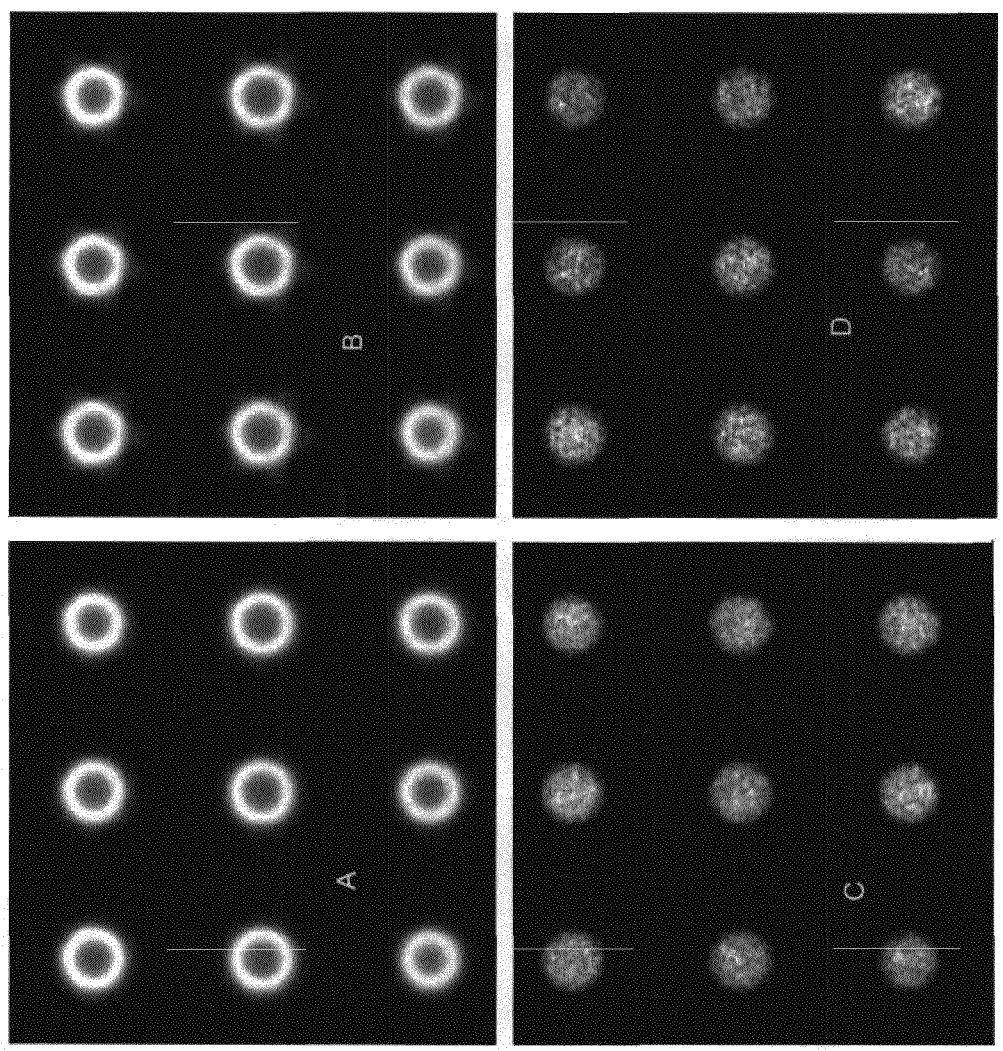
FIGS. 10A-10D illustrate simulation results comparing angular samplings effects and noise effects of the multi-divergent beam systems and the multi-pinhole systems.

In the first comparison study, computer simulated noiseless projections were used. The data were attenuation-less and scatter-free. The purpose of this study was to compare the angular sampling effects for both imaging geometries. In both geometries, the detector partitions were the same; however, their view-angles for each sub-detection-region were different. It is clearly shown in FIG. 10A that 3 detector positions with a multi-divergent-beam collimator provided satisfactory angular sampling; the short axis reconstructions appear as circular rings. On the other hand, the same 3 detector positions with a multi-pinhole collimator did not provide sufficient angular sampling; the circular rings became a little hexagon-like and the background has artifacts in the shape of a star (see FIG. 10B).

In the second comparison study (see FIGS. 10C and 10D), computer simulated noisy projections were used. When the Poisson noise was added to the projections, the sensitivity gain of 2 of the divergent-beam system over the pinhole system was incorporated. The purpose of this second study was to compare the noise effects for both imaging geometries. A uniform spherical phantom of radius 6 cm was used so that it was easier to calculate the noise standard deviation over the center region of the object. It was assumed that both systems had the same scanning time (of approximately 7 minutes with the patient cardiac Tc-99 m dose). The multi-divergent-beam system had a total photon count of 339439, and the multi-pinhole system had a total photon count of 155480. An inscribed cube inside the sphere was used to evaluate the mean and standard deviation of the reconstructed image. The normalized standard deviation (i.e. standard deviation divided by the mean) was 0.12 for the divergent-beam system and was 0.16 for the pinhole system.

There are many approaches to designing a multi-divergent-beam collimator. One approach is to design each divergent zone independently which usually results in a very expensive fabrication cost. Some embodiments provide a novel and economical approach based on a cone-beam collimator.

In order to illustrate the idea, we first use a one-dimensional (1D) example, where the cone-beam collimator degenerates into a fan-beam collimator as shown in FIG. 6. First, we turn the collimator upside down, and the convergent-beam collimator becomes a divergent-beam collimator. Second, we partition the collimator into multiple sections (or zones), and label them as a, b, and c. Third, we cut the sections. Fourth, we rearrange and attach them in a reversed order: c, b, and a. This procedure is illustrated and discussed previously with respect to FIGS. 3A-3E.

If the original convergent-beam collimator has a focal-length f, then such a converted multi-divergent-beam collimator will have a common field-of-view that has a distance f away from the center of the collimator. In other words, if it is sought to design a multi-divergent-beam collimator with the center of the ROI at a distance B from the collimator, first we need to fabricate a convergent-beam collimator that has a focal-length B, then we cut, rearrange, and glue to construct a multi-divergent-beam collimator.

Figure 5B:
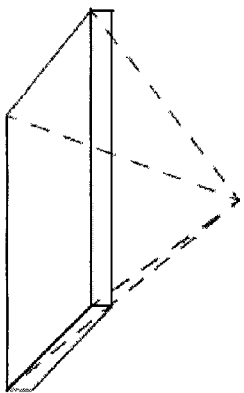
Figure 5C:
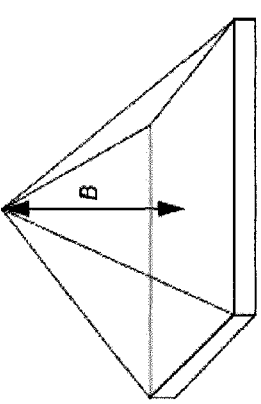
Figure 5D:
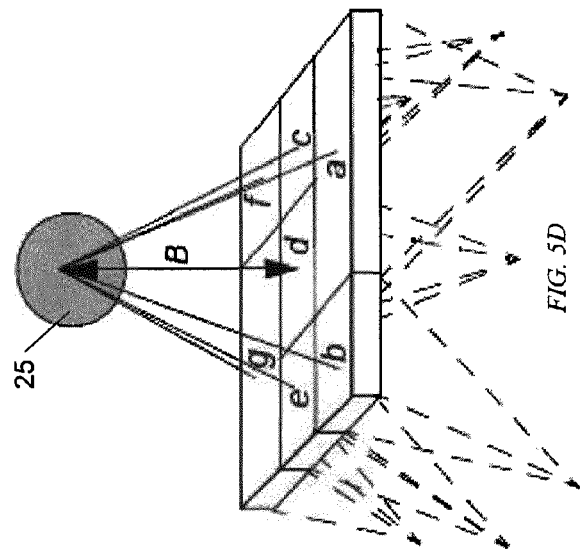

The fabrication of a practical two-dimensional (2D) collimator can follow the same procedure as illustrated above. That is, we start with a regular cone-beam collimator of focal-length, B, then we partition and cut the collimator into sections, finally we rearrange the sections in the reversed order and couple them together as illustrated in FIGS. 5A-5B.

Those skilled in the art will recognize that the present teachings are amenable to a variety of modifications and/or enhancements. For example, although the above-described collimator is discussed for use in a SPECT system it can be used in other types of nuclear medical imaging applications.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

What is claimed is:

1. A method of constructing a multi-divergent beam collimator, the method comprising:
    partitioning a convergent cone-beam collimator into a plurality of ordered regions;
    separating members of the plurality of ordered regions from each other; and
    reassembling in a substantially reversed order the separated members of the plurality of ordered regions, such that the collimator is configured to act as a multi-divergent beam collimator.

2. The method of claim 1, wherein the partitioning comprises partitioning the cone-beam collimator into regions having substantially equal dimensions.

3. The method of claim 1, wherein the partitioning comprises partitioning the cone-beam collimator into regions having different dimensions.

4. The method of claim 1, wherein a plurality of outer regions of the ordered regions have dimensions larger than a plurality of central regions.

5. The method of claim 1, wherein the partitioning comprises portioning the cone-beam collimator into a 3-by-3 array of ordered regions.

6. The method of claim 1, wherein the partitioning comprises portioning the cone-beam collimator into a 2-by-3-by-2 array of ordered regions.

7. An apparatus comprising:
    a plurality of ordered sections of a convergent cone-beam collimator reassembled in a substantially reversed order relative to the ordering of the sections of the cone-beam collimator, wherein the collimator is positionable to function as a multi-divergent-beam collimator.

8. The apparatus of claim 7, wherein each of the sections has substantially similar dimensions.

9. The apparatus of claim 7, wherein some of the plurality of sections have dimensions different from others of the plurality of sections.

10. The apparatus of claim 7, wherein a plurality of outer regions of the ordered regions sections have dimensions larger than those of a plurality of central regions.

11. The apparatus of claim 7, wherein the plurality of sections are portioned into a 3-by-3 array of ordered regions.

12. The apparatus of claim 7, wherein the plurality of sections are portioned into a 2-by-3-by-2 array of ordered regions.

13. A single photo emission computed tomography (SPECT) system, comprising:
    a camera comprising a detector and a collimator, the collimator comprising a plurality of ordered sections of a convergent cone-beam collimator reassembled in a substantially reversed order relative to the ordering of sections of in the cone-beam collimator, wherein the collimator is positionable to function as a multi-divergent beam collimator; and
    a computing system in communication with the camera, the computing system receiving measurements from the camera and processing the received measurements.

14. The SPECT system of claim 13, wherein the camera is substantially stationary.

15. The SPECT system of claim 13, wherein each of the sections has substantially similar dimensions.

16. The SPECT system of claim 13, wherein some of the sections have different dimensions.

17. The SPECT system of claim 13, wherein a plurality of outer regions of the ordered sections have dimensions larger than those of a plurality of central regions.

18. The SPECT system of claim 13, wherein the plurality of sections are portioned into a 3-by-3 array of ordered regions.

19. The SPECT system of claim 13, wherein the plurality of sections are portioned into a 2-by-3-by-2 array of ordered regions.

* * * * *